(12) United States Patent
Austin et al.

(10) Patent No.: US 11,004,548 B1
(45) Date of Patent: May 11, 2021

(54) SYSTEM FOR PROVIDING DE-IDENTIFIED MORTALITY INDICATORS IN HEALTHCARE DATA

(71) Applicant: Universal Patient Key, Inc., Sterling, MA (US)

(72) Inventors: Joseph Austin, Sterling, MA (US); Shahir Kassam-Adams, Lovingston, VA (US); Jason A. LaBonte, Natick, MA (US); Paul Bayless, Burke, VA (US)

(73) Assignee: Datavant, Inc., San Francisco, CA (US)

( * ) Notice: Subject to any disclaimer, the term of this patent is extended or adjusted under 35 U.S.C. 154(b) by 174 days.

(21) Appl. No.: 16/135,972

(22) Filed: Sep. 19, 2018

Related U.S. Application Data

(60) Provisional application No. 62/561,032, filed on Sep. 20, 2017.

(51) Int. Cl.
*G16H 10/60* (2018.01)
*H04L 9/32* (2006.01)
*G06F 16/242* (2019.01)
*G06F 16/22* (2019.01)

(52) U.S. Cl.
CPC ......... *G16H 10/60* (2018.01); *G06F 16/2228* (2019.01); *G06F 16/244* (2019.01); *H04L 9/3226* (2013.01)

(58) Field of Classification Search
CPC combination set(s) only.
See application file for complete search history.

(56) References Cited

U.S. PATENT DOCUMENTS

| | | |
|---|---|---|
| 5,892,900 A | 4/1999 | Ginter et al. |
| 6,397,224 B1 | 5/2002 | Zubeldia et al. |
| 6,732,113 B1 | 5/2004 | Ober et al. |
| 6,734,886 B1 | 5/2004 | Hagan et al. |
| 6,804,787 B2 | 10/2004 | Dick |
| 7,120,928 B2 | 10/2006 | Sheth et al. |

(Continued)

OTHER PUBLICATIONS http://mist-deid.sourceforge.net/ "MIST—The MITRE Identification Scrubber Toolkit".

(Continued)

*Primary Examiner* — Elaine Gort
*Assistant Examiner* — Shyam M Goswami
(74) *Attorney, Agent, or Firm* — Morse, Barnes-Brown & Pendleton, P.C.; Sean D. Detweiler, Esq.

(57) ABSTRACT

A method and system for identifying individuals in a healthcare dataset who are likely deceased without exposing protected health information to users. The present invention assembles mortality data from different sources, de-identifies this data by removing or modifying all elements regarded as protected health information, and adds a unique encrypted person token to each record. The tokenized mortality data is merged with other healthcare data sets that have likewise been de-identified and tokenized by matching the unique person tokens in data sets against each other. The resulting merged data sets include an indicator of mortality, a uniqueness score giving the likelihood that the person token is unique, and a death validity score giving a measure of confidence that the person is actually deceased.

16 Claims, 9 Drawing Sheets

(56) References Cited

U.S. PATENT DOCUMENTS

| | | | |
|---|---|---|---|
| 7,269,578 B2 | 9/2007 | Sweeny | |
| 7,376,677 B2 | 5/2008 | Ober et al. | |
| 7,428,706 B2 | 9/2008 | Hagan et al. | |
| 7,519,591 B2 | 4/2009 | Landi et al. | |
| 7,526,485 B2 | 4/2009 | Hagan et al. | |
| 7,543,149 B2 | 6/2009 | Ricciardi et al. | |
| 7,587,366 B2 | 9/2009 | Grim, III et al. | |
| 7,668,835 B2 | 2/2010 | Judd et al. | |
| 7,711,120 B2 | 5/2010 | Kimmel et al. | |
| 7,792,517 B2 | 9/2010 | Mowry et al. | |
| 7,827,234 B2 | 11/2010 | Eisenburger et al. | |
| 7,865,376 B2 | 1/2011 | Ober | |
| 7,945,048 B2 | 5/2011 | Ricciardi et al. | |
| 8,024,339 B2 | 9/2011 | Barker et al. | |
| 8,037,052 B2 | 10/2011 | Kariathungal et al. | |
| 8,042,193 B1 | 10/2011 | Pilouras | |
| 8,069,053 B2 | 11/2011 | Gervais et al. | |
| 8,090,595 B2 | 1/2012 | Hartman | |
| 8,121,984 B2 | 2/2012 | Barbieri | |
| 8,176,334 B2 | 5/2012 | Vainstein | |
| 8,275,850 B2 | 9/2012 | Kohan et al. | |
| 8,296,299 B2 | 10/2012 | Haskell et al. | |
| 8,296,341 B2 | 10/2012 | Hagan et al. | |
| 8,341,427 B2 | 12/2012 | Auradkar et al. | |
| 8,355,923 B2 | 1/2013 | Gervais et al. | |
| 8,364,969 B2 | 1/2013 | King | |
| 8,381,287 B2 | 2/2013 | Trotter | |
| 8,473,452 B1 | 6/2013 | Ober et al. | |
| 8,494,874 B2 | 7/2013 | Green, III et al. | |
| 8,560,456 B2 | 10/2013 | Williams | |
| 8,566,113 B2 | 10/2013 | Friedlander et al. | |
| 8,577,933 B2 | 11/2013 | Evenhaim | |
| 8,589,437 B1 | 11/2013 | Khomenko et al. | |
| 8,661,249 B2 | 2/2014 | Guarraci et al. | |
| 9,292,707 B1 | 3/2016 | Fontecchio | |
| 9,614,814 B2 | 4/2017 | Fontecchio | |
| 9,830,476 B2 | 11/2017 | Fontecchio | |
| 10,255,456 B2 | 4/2019 | Guglani et al. | |
| 2002/0073138 A1 | 6/2002 | Gilbert et al. | |
| 2002/0173971 A1 | 11/2002 | Stirpe et al. | |
| 2006/0053032 A1 | 3/2006 | Weiler et al. | |
| 2007/0162377 A1 | 7/2007 | Williams | |
| 2008/0147554 A1 | 6/2008 | Stevens et al. | |
| 2009/0106550 A1 | 4/2009 | Mohamed | |
| 2009/0287502 A1 | 11/2009 | Roberts et al. | |
| 2010/0042583 A1 | 2/2010 | Gervais et al. | |
| 2010/0070306 A1 | 3/2010 | Dvorak et al. | |
| 2010/0094758 A1 | 4/2010 | Chamberlain et al. | |
| 2010/0114607 A1 | 5/2010 | Kress | |
| 2010/0205009 A1 | 8/2010 | Kostoff | |
| 2010/0211781 A1 | 8/2010 | Auradkar et al. | |
| 2010/0223467 A1 | 9/2010 | Dismore et al. | |
| 2010/0256994 A1 | 10/2010 | Eisenburger et al. | |
| 2011/0191245 A1 | 8/2011 | Ricciardi et al. | |
| 2012/0036360 A1 | 2/2012 | Bassu et al. | |
| 2012/0116800 A1 | 5/2012 | McCallie et al. | |
| 2012/0124637 A1 | 5/2012 | Dunaway | |
| 2012/0204032 A1 | 8/2012 | Wilkins et al. | |
| 2012/0226916 A1 | 9/2012 | Hahn et al. | |
| 2012/0316898 A1 | 12/2012 | Levitt et al. | |
| 2013/0117126 A1 | 5/2013 | Coppinger | |
| 2013/0117128 A1 | 5/2013 | Coppinger | |
| 2013/0246097 A1 | 9/2013 | Kenney et al. | |
| 2013/0304504 A1 | 11/2013 | Powel | |
| 2013/0304542 A1 | 11/2013 | Powel | |
| 2013/0346104 A1 | 12/2013 | Pillai | |
| 2014/0013452 A1 | 1/2014 | Aissi et al. | |
| 2014/0040308 A1 | 2/2014 | Ober et al. | |
| 2014/0041047 A1 | 2/2014 | Jaye et al. | |
| 2014/0108049 A1 | 4/2014 | Fuhrmann et al. | |
| 2014/0108258 A1 | 4/2014 | Williams | |
| 2014/0122873 A1 | 5/2014 | Deutsch et al. | |
| 2015/0095243 A1* | 4/2015 | Eiler | G06Q 10/10 705/312 |
| 2015/0095252 A1 | 4/2015 | Mattsson et al. | |
| 2015/0149208 A1 | 5/2015 | Lynch et al. | |
| 2016/0110648 A1* | 4/2016 | Baveja | G06N 5/04 706/52 |
| 2016/0147945 A1 | 5/2016 | MacCarthy et al. | |
| 2016/0267238 A1 | 9/2016 | Nag | |
| 2016/0275309 A1 | 9/2016 | Austin et al. | |
| 2016/0344544 A1* | 11/2016 | Biesinger | H04L 9/088 |
| 2017/0103179 A1* | 4/2017 | Jiao | G16H 10/20 |
| 2017/0243028 A1 | 8/2017 | LaFever et al. | |

OTHER PUBLICATIONS

Non-Final Office Action from U.S. Appl. No. 16/382,447, dated Dec. 16, 2020.

Non-Final Office Action for U.S. Appl. No. 16/382,462, dated Oct. 29, 2020.

Notice of Allowance from U.S. Appl. No. 15/045,605, dated Oct. 14, 2020.

Non-Final Office Action for U.S. Appl. No. 16/684,541, dated Feb. 18, 2021.

* cited by examiner

SYSTEM FOR PROVIDING DE-IDENTIFIED MORTALITY INDICATORS IN HEALTHCARE DATA

CROSS-REFERENCE TO RELATED APPLICATION(S)

This application claims priority to, and the benefit of, U.S. Provisional Application No. 62/561,032, filed Sep. 20, 2017, for all subject matter common to both applications. The disclosure of said provisional application is hereby incorporated by reference in its entirety.

FIELD OF THE INVENTION

The present invention relates to providing healthcare records associated with deceased individuals without exposing protected healthcare information of the deceased individual. In particular, the present invention relates to a system and method configured to provide an improvement in computer capabilities that enables a computer system to merge data sets without compromising data privacy and security that computers were not capable of performing before using existing data replication techniques, by implementing specific means, rules, and functions that remove protected health information from mortality reports from public and private sources and replace each individual's personal information with a unique encrypted token (or "key") that allows that individual record to be matched to a de-identified and tokenized healthcare data set for the deceased individual.

BACKGROUND

Generally, conventional healthcare data systems are limited in their ability to identify deceased individuals from individual records in healthcare data sets. One reason for the lack of data related to deceased individuals is the fact that publically-available mortality data contains protected health information ("PHI") or personal identification information (PII) (e.g., names, addresses, dates of birth, dates of death, social security numbers, etc.). It is a potential Health Insurance Portability and Accountability Act (HIPAA) violation to incorporate PHI elements into a healthcare data set. Accordingly, to be compliant with government regulations, all PHI data elements must be removed and/or de-identified before being incorporated into any healthcare data set. However, once PHI data elements are removed from record, users have no way to understand which individuals in the data set match the de-identified individuals who are deceased. Therefore, current systems and methods do not attempt to incorporate mortality data into healthcare data sets.

SUMMARY

There is a need for improvements for enabling healthcare data sets within healthcare records of deceased individuals to be accessible and useable without exposing protected healthcare information of the deceased individual. The present invention is directed toward further solutions to address this need, in addition to having other desirable characteristics. Specifically, the present invention provides an advancement made in computer technology consists of improvements defined by logical structures and processes directed to a specific implementation of a solution to a problem in software, data structures and data management, wherein the existing data structure technology relies upon unacceptable reproduction of protected health information, personal identification information, or other private information to transmit data for data processing purposes that cannot meet or be used under current HIPAA requirements and other laws, regulations, rules and standards governing privacy and data security, by providing a system and method in which mortality data is matched with individual records in a healthcare data set without exposing PHI. In particular, the present invention provides a system and method that creates a specific, non-abstract improvement to computer functionality, that previously could not be merged without exposing PHI and PII, that de-identifies data by removing protected health information and personal identification information from the record, adds a unique encrypted person token to each record, and merges the record with other healthcare data sets that have likewise been de-identified and tokenized by matching the unique encrypted person tokens in data sets to one another, thus maintaining the ability to match disparate data (e.g., mortality data and healthcare data) from disparate sources for a same individual.

In accordance with example embodiments of the present invention, a method for providing de-identified mortality indicators in healthcare data is provided. The method includes aggregating, using a computing device, mortality data records associated with identifiable individuals from at least one data source and merging the aggregated mortality data records into mortality data sets each associated with identifiable individuals. The method also includes assigning a uniqueness score to each mortality data set and assigning a death validity score to each mortality data set. The method further includes de-identifying, using a computing device with data comprising the uniqueness score and the death validity score, the mortality data sets by removing protected health information and personal identification information within the mortality data sets and associating each mortality data set previously associated with an identifiable individual with a unique encrypted person token, which is unique to each individual of the identifiable individuals. The method also includes merging the de-identified mortality data sets with previously de-identified healthcare data sets with unique encrypted person tokens associated therewith and delivering the merged de-identified healthcare data sets in response to receiving, using the computing device, previously de-identified healthcare data sets with unique encrypted person tokens associated therewith, wherein data sets are stored in a location comprising encrypted tokens in place of protected health information and personal identification information and delivering of records associated with identifiable individuals is prevented.

In accordance with aspects of the present invention, the merging comprises matching unique encrypted person tokens of mortality data sets with the unique encrypted person tokens of the previously de-identified healthcare data sets. Each of the mortality data sets can includes a unique encrypted person token, an indicator of mortality, a uniqueness score, and a death validity score. Each of the mortality data sets can also include a cause of death indicator. Each of the mortality data sets can also include a gender probability score. The uniqueness score can indicate a likelihood that the unique encrypted person token for a given mortality data set is unique and the death validity score can indicate a confidence value that an individual associated with a given mortality data set is actually deceased. Determining the uniqueness score can include extracting identification information from the mortality data sets associated with identifiable individuals, querying the identification information against a population data set and a social data set, identifying matches of the identification information occurring within the population data set or the social data set, calculating the uniqueness score by dividing one by the number of identified matches, and appending the uniqueness score to a mortality data set associated with the individual.

In accordance with aspects of the present invention, the determining the death validity score can also include analyzing mortality data sets associated with identifiable individuals, identifying matches of the identification information occurring within the mortality data sets, identifying a total number of indications of an identifiable individual as being deceased, dividing the total number of indications of an identifiable individual as being deceased by a total number of matches for the identifiable individual occurring within the mortality data sets to determine a probability percentage of the at least one data source that indicates that the identifiable individual is deceased, appending the probability percentage to a mortality data set of the mortality data sets that is associated with the individual as the death validity score for the individual. Determining the uniqueness score can also include a rule based function that transforms the probability percentage into a probability level based on the probability percentage, the probability level having a non-quantitative descriptive range.

In accordance with aspects of the present invention, the at least one data source can include one or more of a social security death master file, a lifestyle data for gender, and obituary data. The death validity score can be a quantitative statistical score. The death validity score can be a qualitative flag.

In accordance with aspects of the present invention, the delivering of records associated with identifiable individuals can be prevented by segregating de-identified and tokenized data sets from any data base or data storage containing identifiable information by storing in a specialized database for de-identified and tokenized data sets only and encoding access and permission restrictions allowing transmission requested data from the specialized database only.

In accordance with example embodiments of the present invention, a system is provided. The system includes a computing device and one or more databases containing previously de-identified healthcare data sets with encrypted person tokens and a data aggregation module configured to aggregate data records with protected health information included therein from a plurality of data sources. The system also includes a merging module configured to transform all of the data records associated with identifiable individuals into mortality data sets, each of the mortality data sets uniquely associated with each of the identifiable individuals. The de-identification module is configured to remove the protected health information from the mortality data sets to create de-identified mortality data sets and create an encrypted person token based on the removed protected health information, wherein the encrypted person token is uniquely associated with an individual previously associated with the removed protected health information. The merging module is configured to merge the de-identified mortality data sets with de-identified healthcare data sets based on matching encrypted person tokens associated therewith. The resulting merged data sets include an indicator of mortality, a match probability score giving the likelihood that the unique person token is unique, and a death validity score giving a measure of confidence that the person is actually deceased and is stored in a location segregated from protected health information and personal identification information, wherein delivering of records associated with identifiable individuals is prevented.

In accordance with aspects of the present invention, the system can isolate de-identified and tokenized data sets from any data base or data storage containing identifiable information by storing in a specialized database for de-identified and tokenized data sets only and encoding access and permission restrictions allowing transmission requested data from the specialized database only.

In accordance with example embodiments of the present invention, a system is provided. The system includes one or more databases containing data sets. The data sets include de-identified mortality data sets with protected health information removed, the de-identified mortality data sets having an association with each mortality data set previously associated with an identifiable individual with a unique encrypted person token, which is unique to each individual of the identifiable individuals. The data sets also include previously de-identified healthcare data sets with unique encrypted person tokens associated therewith. The de-identified mortality data sets are merged with the previously de-identified healthcare data sets with unique encrypted person tokens associated therewith and the resulting merged data sets include an indicator of mortality, a match probability score giving the likelihood that the unique person token is unique, and a death validity score giving a measure of confidence that the person is actually deceased.

BRIEF DESCRIPTION OF THE FIGURES

These and other characteristics of the present invention will be more fully understood by reference to the following detailed description in conjunction with the attached drawings, in which.

DETAILED DESCRIPTION

Figure 1:
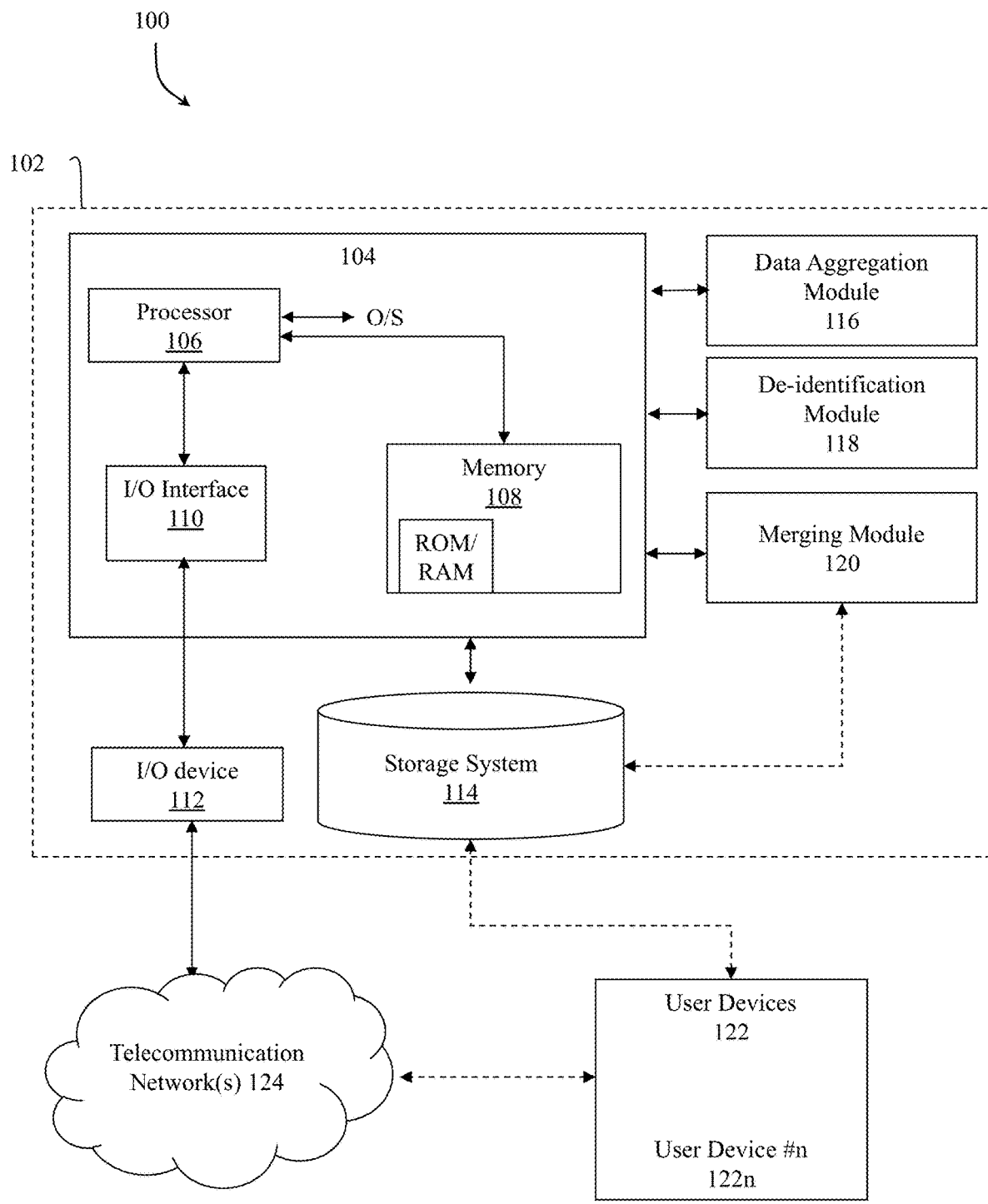
FIG. 1 is a diagrammatic illustration of a system for implementation of the present invention.

An illustrative embodiment of the present invention relates to a specific system and method with means that improves the existing technology by reciting specific structures, functions and steps that accomplish the desired result through an inventive arrangement by combining mortality data with healthcare data in a manner that does not violate HIPAA or other privacy related regulations that restrict PHI or PII. In particular, mortality data is aggregated from different sources (e.g., Social Security Death Master File (SSDMF) weekly updates, obituary data, etc.), the mortality data is de-identified by removing or modifying all elements regarded as protected health information, and a unique encrypted person token is added to each record. The "tokenized" mortality data is merged with other healthcare data sets that have been de-identified and tokenized in a similar process, that uses a combined order of specific incorporated rules and functions, not mere use of the computer and existing data processing technology, that improves the existing data management technological processes that renders mortality information and health care information into a specific format that is then used and applied to create desired results of data sets that can be used together in an encrypted and privacy preserving manner. Specifically, the healthcare data sets are merged with the mortality data by matching the unique encrypted person tokens associated with each data record with one another and the data records with matching unique encrypted person tokens are merged together. Using the system and method of the present invention provides a specific, non-abstract improvement to computer functionality that enables "individuals" (e.g., de-identified healthcare records) in a healthcare data set to be marked as potentially deceased without exposing protected health information or personal identification data. This in turn enables databases or data structures containing health care data sets, operated by separate, potentially unrelated entities, to query, receive, and incorporate (including by merging) data sets including mortality data or related data in a separate database or data structure that ordinarily would not be capable of interacting due to the above discussed restrictions on combining such data and the existing technological requirements of reproducing data within data structures in order to preserve unique identifiers and data used to accurately correlate or match data based on association with an underlying entity.

The mortality data sets, created by the present invention, contain the de-identified unique encrypted person tokens, an indicator of mortality of the individual previously identified in the data record, a uniqueness score, and a death validity score. This transformed data functions differently than, and achieves benefits over, conventional database structures and data therein, providing increased flexibility, and the ability to combine otherwise un-combinable data sets. To improve accuracy without sacrificing privacy and data security, the uniqueness score in the mortality data sets provide a likelihood value (or probability) that the encrypted person token is unique to a particular individual. In other words, the uniqueness score is a probability or confidence indicator as to how likely an individual is the same individual in a record. The uniqueness score quantifies the likelihood value through a determination as to how many individuals share the same information. For example, for the uniqueness score, the present invention determines how many John Doe's share the same birthday and live in the same city/state. The death validity score provides a level of confidence value that the individual is actually deceased. As a result, the uniqueness score provides statistical information to a user for how likely that the mortality set matches with a healthcare set(s) is actually the same individual originally associated with both original data records because the information in the mortality data and healthcare data are provided by different sources. Similarly, the quantitative death validity score provides statistical information about how likely it is that an individual originally associated with a healthcare set(s) is actually deceased. Alternatively, the death validity score can be represented as a qualitative flag indicating how likely it is that an individual originally associated with a healthcare set(s) is actually deceased. For example, if there are two John Does sharing the same birthday, residence, etc. and a mortality data record indicates there is a deceased John Doe matching that information, the death validity score indicates how likely that the John Doe originally associated with a healthcare set is the deceased John Doe.

Once the mortality data sets and healthcare data sets are merged, a user can perform analysis of anonymous healthcare data with the added benefit of the deceased indications for the de-identified individuals originally associated with the healthcare records. This functionality provides many added benefits not previously available to healthcare practitioners. For example, mortality data is critical to properly understanding the effectiveness and safety of clinical treatment; marking deceased status for de-identified patients in healthcare data is critical. As would be appreciated by one skilled in the art, the mortality data sets are not limited to individuals who are/may be deceased but can also be extended to individuals associated with a particular disease (e.g., morbidity data) without departing from the scope of the present invention. Additionally, the present invention can be utilized to prevent identity theft, fraud, and facilitates proper billing and collections for deceased patients. The de-identification of healthcare data sets and mortality data sets provided by the present invention enables mortality indicators to be merge-able with the healthcare data sets in such a way that data sets from disparate sources but relating to a same individual can be matched up and associated with each other without the exposure of PHI.

FIGS. 1 through 9, wherein like parts are designated by like reference numerals throughout, illustrate an example embodiment or embodiments of improved operation for the inclusion of deceased status from the de-identified mortality data in healthcare data sets, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed in a manner still in keeping with the spirit and scope of the present invention.

FIG. 1 depicts an illustrative system 100 for implementing the steps in accordance with the aspects of the present invention. In particular, FIG. 1 depicts a system 100 including a de-identification system 102. In accordance with an example embodiment, the de-identification system 102 is a combination of hardware and software configured to carry out aspects of the present invention. In particular, the de-identification system 102 is a computing system with specialized software and databases designed for providing a method for de-identifying and tokenizing healthcare records, de-identifying and tokenizing mortality records, and merging the de-identified healthcare and mortality records in a manner to enable a user to identify potentially deceased individuals within healthcare records without revealing PHI or PII about the individual. The specialized software and databases or data structures function differently than, and achieves benefits over, conventional databases and data structures, providing a specific implementation of a solution to the persist problem of the need to combine data sets that are prohibited from combination due to resulting breaches in privacy and data security. For example, the de-identification system 102 can be software installed on a computing device 104, a web based application provided by a computing device 104 which is accessible by computing devices (e.g., the user devices 122), a cloud based application accessible by computing devices, or the like. The combination of hardware and software that make up the de-identification system 102 are specifically configured to provide a technical solution to a particular problem utilizing an unconventional combination of steps/operations to carry out aspects of the present invention. In particular, the de-identification system 102 is designed to execute a unique combination of steps to provide a novel approach to identifying individuals (or records for individuals) in a healthcare dataset who are likely deceased without exposing protected health information for those individuals.

In accordance with an example embodiment of the present invention, the de-identification system 102 can include a computing device 104 having a processor 106, a memory 108, an input output interface 110, input and output devices 112 and a storage system 114. Additionally, the computing device 104 can include an operating system configured to carry out operations for the applications installed thereon. As would be appreciated by one skilled in the art, the computing device 104 can include a single computing device, a collection of computing devices in a network computing system, a cloud computing infrastructure, or a combination thereof. Similarly, as would be appreciated by one of skill in the art, the storage system 114 can include any combination of computing devices configured to store and organize a collection of data. For example, storage system 114 can be a local storage device on the computing device 104, a remote database facility, or a cloud computing storage environment. The storage system 114 can also include a database management system utilizing a given database model configured to interact with a user for analyzing the database data.

Continuing with FIG. 1, the de-identification system 102 can include a combination of core components to carry out the various functions of the present invention. In accordance with an example embodiment of the present invention, the de-identification system 102 can include a data aggregation module 116, a de-identification module 118, and a merging module 120. As would be appreciated by one skilled in the art, the data aggregation module 116, the de-identification module 118, and the merging module 120 can include any combination of hardware and software configured to carry out the various aspects of the present invention. In particular, each of the data aggregation module 116, the de-identification module 118, and the merging module 120 are configured to provide users with a system to search data streams for particular content.

In accordance with an example embodiment of the present invention, the system 100 can include a plurality of user devices 122 configured to communicate with the de-identification system 102 over a telecommunication network(s) 124. The de-identification system 102 can act as a centralized host, for the user devices 122, providing the functionality of the modules 116, 118, 120, sharing a secured network connection. As would be appreciated by one skilled in the art, the plurality of user devices 122 can include any combination of computing devices, as described with respect to the de-identification system 102 computing device 104. For example, the computing device 104 and the plurality of user devices 122 can include any combination of servers, personal computers, laptops, tablets, smartphones, etc. In accordance with an example embodiment of the present invention, the computing devices 104 and user devices 122 are configured to establish a connection and communicate over telecommunication network(s) 124 to carry out aspects of the present invention. As would be appreciated by one skilled in the art, the telecommunication network(s) 124 can include any combination of known networks. For example, the telecommunication network(s) 124 may be combination of a mobile network, WAN, LAN, or other type of network. The telecommunication network(s) 124 can be used to exchange data between the computing devices 104, user devices 122, exchange data with the storage system 114, and/or to collect data from additional sources.

Figure 2:
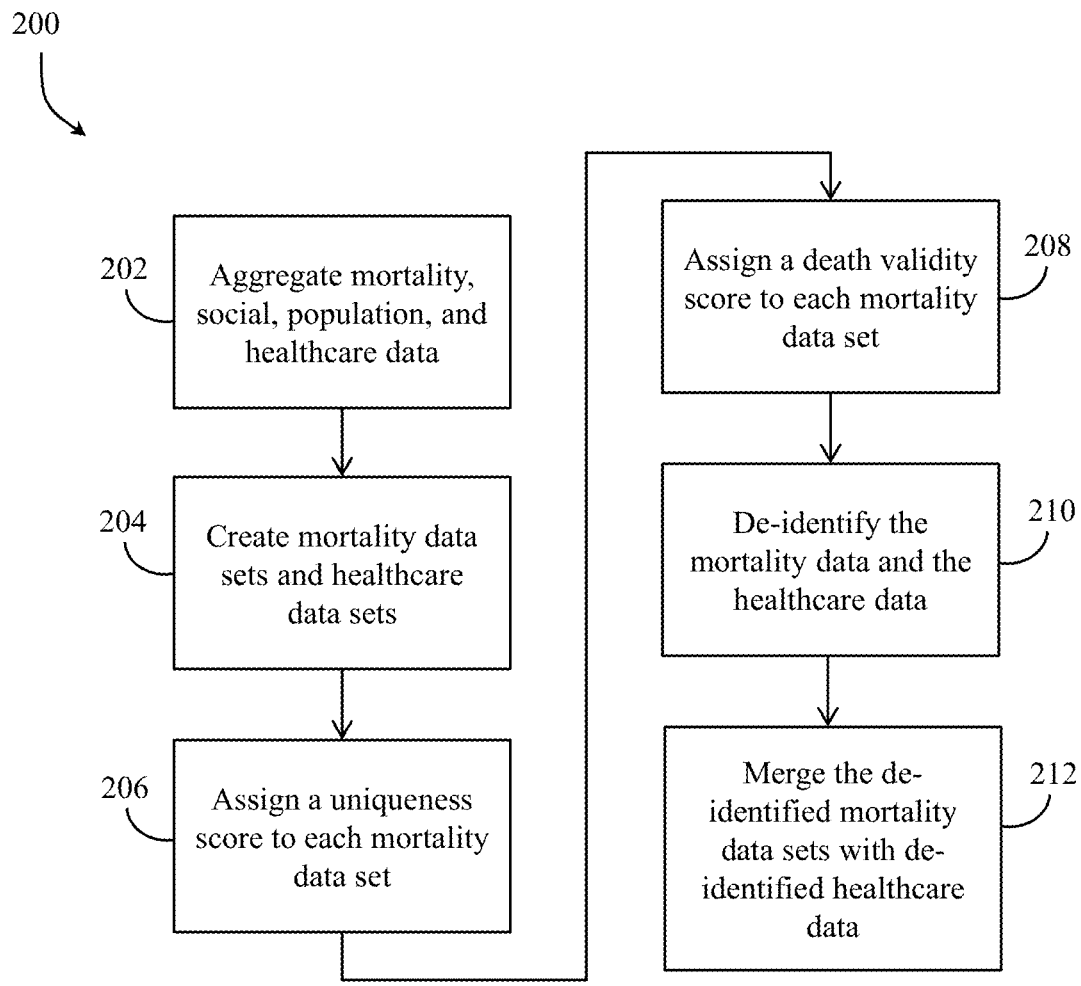
FIG. 2 is a flowchart depicting the process of operation of the system of the present invention.

In operation, the de-identification system 102 assembles mortality data from different sources (e.g., Social Security Death Master File weekly updates, obituary data, etc.), de-identifies this data by removing or modifying all elements regarded as protected health information, and adds a unique encrypted person token (derived from the PHI or PII) to each record. In accordance with an example embodiment of the present invention, data records from other data sources are also aggregated and utilized to supplement the mortality data. For example, population data and social data records including, but not limited to, birth records/announcements, wedding engagements/ceremonies, social media data, etc. can be aggregated and merged with the mortality data. As would be appreciated by one skilled in the art, the de-identification system 102 can also assemble and include morbidity data. The morbidity data can be aggregated from any combination of sources including the sources providing the mortality data. For example, the morbidity data can be found in social media data (e.g., patient support groups, discussions on social media, etc.), other insurance/worker's comp data for injuries, membership in groups, registries, retail purchasing data (over the counter purchases from pharmacies, amazon, etc. for disease or injury-related items), clinical trial participation, etc. As would be appreciated by one skilled in the art, after data records from other data sources are merged with the mortality data and morbidity data, all PHI and PII are removed from the merged mortality data. The "tokenized" mortality data is merged with other healthcare data sets that have similarly been de-identified and tokenized by matching the unique encrypted person tokens in each data set with one another. In this way, individuals in healthcare data sets can be marked as potentially deceased without ever exposing or using protected health information. FIG. 2 depicts an exemplary process 200 outlining the operation of the de-identification system 102, in accordance with the present invention.

At step 202 of the process 200, the aggregation module 116 aggregates a combination of healthcare data records, social data records, population data, and mortality records from a combination of publicly available and private sources. In accordance with an example embodiment of the present invention, the data aggregation module 116 collects and stores (e.g., in the storage system 114) a combination of healthcare data, social data records, mortality data, and population data.

The healthcare data includes healthcare records that are associated with individual patients. For example, healthcare records include electronic healthcare records for a patient including information related to physician visits, laboratory tests, hospitalizations, prescriptions, etc. Mortality data includes mortality data records related to a deceased status of an individual. For example, mortality data records indicating a deceased status of an individual can include records such as a death certificate, a notification to social security administration, an obituary, etc. The social data and population data includes any compilation of data about a population of individuals that can be useful with mortality and healthcare related data. The population data can include data sets (e.g., census, surveys, etc.) that contain the same fields as the fields used to create tokens in the de-identification process (names, dates of birth, gender, sometimes zip, etc.), as discussed in greater detail herein. The social data can include data sets birth records/announcements, wedding engagements/ceremonies, social media account data, etc.

The data aggregation module 116 can aggregate the healthcare data, mortality data, social data, and population data from any combination of publicly and privately accessible data sources. For example, the healthcare data can be obtained from healthcare providers through access to private databases and mortality data, social data and population data can be obtained from publically-available databases. As would be appreciated by one skilled in the art, the data aggregation module 116 can obtain the various data records through any combination of methods and systems known in the art.

At step 204 of the process 200, the merging module 120 creates mortality data sets and healthcare data sets from the aggregated mortality data records and healthcare data records. In particular, the data aggregation module 116 combines mortality data records from different data sources that may be associated with the same individual into a single mortality data set, as discussed in greater detail with respect to FIG. 3. The healthcare data records for the same individual are similarly combined into healthcare data sets. In accordance with an example embodiment of the present invention, data records from the other data sources can be merged with the mortality data sets and healthcare data sets to create more complete data sets. For example, the name and gender information from the social data and population data can be merged with the mortality data sets and healthcare data sets to fill in gaps of information (e.g., date of birth, gender, etc.). As would be appreciated by one skilled in the art, the mortality data sets will include data unique from the data included within the healthcare data sets. For example, in accordance with an example embodiment, the mortality data sets include an indicator of mortality, a uniqueness score, a cause of death indicator, and a death validity score, which are not traditionally found in healthcare data sets.

At step 206 of the process 200, the data aggregation module 116 (e.g., the data aggregation module 116) assigns a uniqueness score to each of the mortality data sets. In particular, the data aggregation module 116 determines a likelihood value that the information provided in each mortality data set is unique to a particular individual, as discussed in greater detail with respect to FIGS. 4 and 5. For example, the data aggregation module 116 determines a probability for how likely that the information included within the mortality data set is unique to single individual. The social data and population data can be utilized by the present invention improve the accuracy of the uniqueness score. For example, data from the social data and population data can be utilized to determine a probability that a particular name (e.g., from a mortality record) is associated with a female or male, which can influence the uniqueness score.

At step 208 of the process 200, the data aggregation module 116 assigns a death validity score to each of the mortality data sets. In particular, the data aggregation module 116 determines a confidence value that an individual associated with the given mortality data set is actually deceased, as discussed in greater detail with respect to FIGS. 4 and 6. For example, the de-identification module 118 determines how likely that the deceased status included within the mortality data set is properly associated with the mortality data set for a particular individual.

At step 210 of the process 200 the de-identification module 118 de-identifies (e.g., removes protected health information) from the healthcare data records and mortality records and replaces the PHI or PII with an encrypted token (or "key") that allows individual records for specific individuals to be matched to one another without revealing any identifying information for that individual, as discussed in greater detail with respect to step 212. In accordance with an example embodiment of the present invention, the de-identification module 118 performs the de-identification of and tokenization of the data sets utilizing the method and system discussed in U.S. patent application Ser. No. 15/045,605 filed on Feb. 17, 2016, incorporated herein by reference. An example implementation of the de-identification process for mortality data is discussed in greater detail with respect to FIG. 7.

At step 212 of the process 200 the de-identification system 102 merges the de-identified mortality data sets with the de-identified healthcare data sets to create healthcare data sets that include mortality data. In accordance with an example embodiment of the present invention, the merging module 120 matches the unique encrypted person tokens of mortality data sets with the unique encrypted person tokens of the de-identified healthcare data sets and merges the fields from each data set to create a single data set. In other words, a de-identified and tokenized mortality data set for an individual can be matched to a likewise de-identified and tokenized healthcare data set for that same individual and the fields for each of the data sets are merged together to create a single data set for that de-identified individual. The new data set includes merged fields from a mortality data set and a healthcare data set and results in a healthcare data set that is flagged with an indication as to how likely the individual associated with the data set is deceased. As would be appreciated by one skilled in the art, multiple mortality data sets can be merged with multiple different healthcare data sets while identifying a level of confidence that the individual in each of the data sets is the same individual (e.g., as discussed in FIGS. 4 and 5). For example, if a mortality data set includes a common first and last name (e.g., John Smith) then there may be multiple healthcare records sharing that same first and last name which will each be merged with the same mortality data set. The resulting data sets will for John Smith each include an indication of a deceased individual. The uniqueness score designation is also applied to convey to a user how common this scenario occurred and thus how likely the individual (e.g., John Smith) is actually deceased. The resulting data sets may be further segregated and isolated from any data base or data storage containing identifiable information, for example by storing in a specialized database for de-identified and tokenized data sets only that encoding access and permission restrictions allowing transmission requested data from the specialized database only.

As would be appreciated by one skilled in the art, the individual steps in process 200 and any of the processes in FIGS. 3-8 can performed in different sequences, through different techniques, and/or merged into single processes or split into smaller processes that can be run serially or in parallel. Additionally, although FIGS. 3-7 are discussed with example implementations specific to mortality data, the processes of FIGS. 3-7 can similarly be applied to healthcare data in combination with the mortality data without departing from the scope of the present invention.

Figure 3:
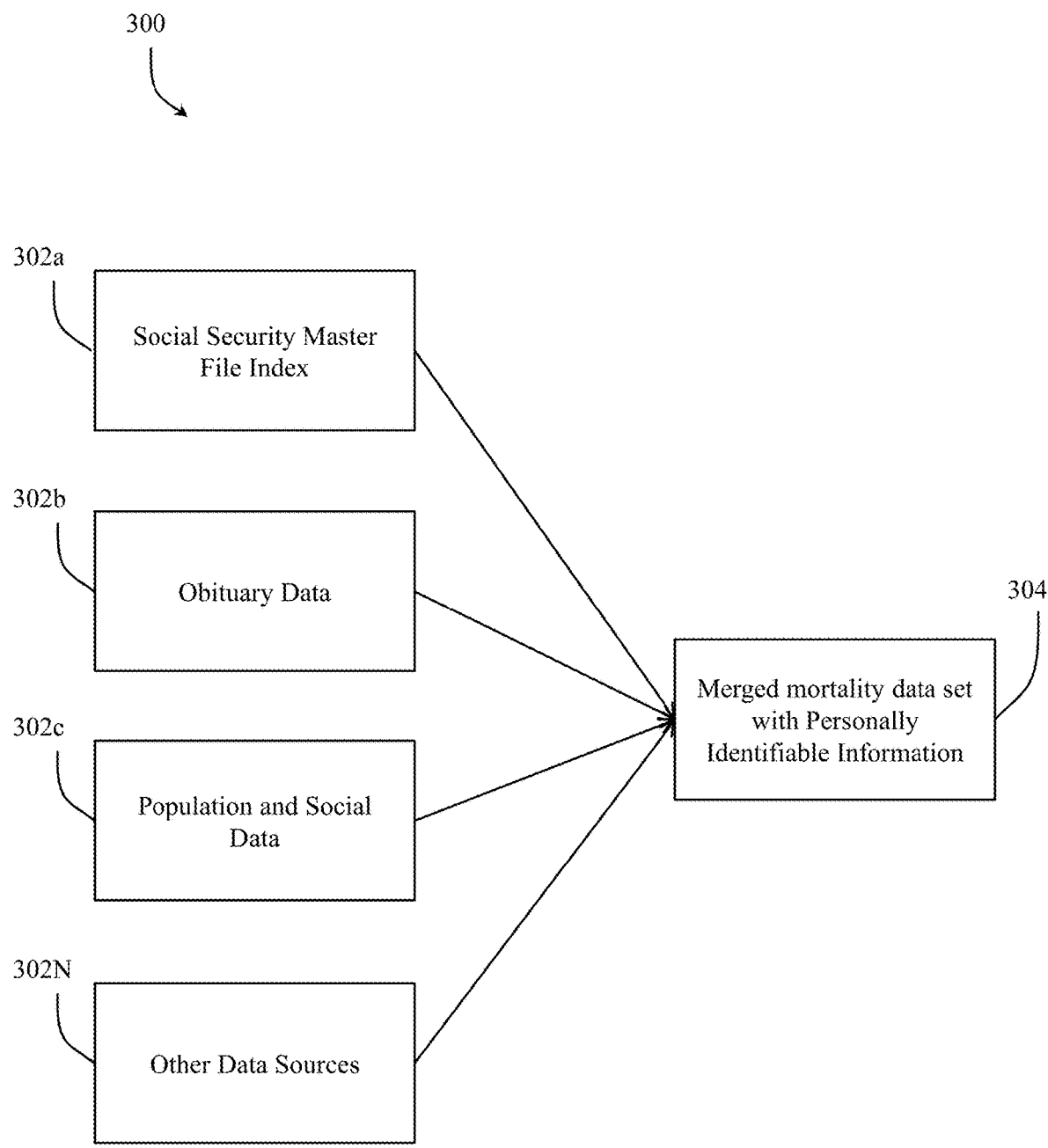
FIG. 3 is a flowchart depicting the aggregation of mortality data in accordance with the present invention.

FIG. 3 illustrates the mortality data aggregation process 300 for obtaining and merging mortality data records (e.g., as discussed with respect to step 202 of FIG. 2). In accordance with an example embodiment of the present invention, the data storage system 114 can include reference to multiple data sources 302a, 302b, 302c that include mortality data records (e.g., Social Security Death Master File (SSDMF), Obituary Data, etc.), and population and social data that are periodically updated. Other data sources 302N may be accessed to supplement the data aggregated from data sources 302a, 302b, 302c. For example, cause of death data can be aggregated from the Center for Disease Control (CDC) and merged with the mortality data set. As would be appreciated by one skilled in the art, N number of data sources 302N can be utilized in accordance with the present invention.

The data aggregation module 116 is configured to update data received from each of the data sources 302a, 302b, 302c, 302N and merge the data to create mortality data sets with personally identifiable information (PII) 304. In particular, the data aggregation module 116 identifies which data records correspond to the same individual and combine the mortality data records to form a mortality data set. For example, the data aggregation module 116 compares various fields from the mortality data records and combine any data records that share identical information over particular fields or combination of fields (e.g., personally identifiable information, PHI, etc.). As would be appreciated by one skilled in the art, different forms of personally identifiable information will require more or less matches to result in a combination to trigger a merging of the data records. For example, mortality data records can be combined when only a data field associated with a social security number is identified as matching. In another example, the data aggregation module 116 may require that multiple data fields, within a mortality record, of at least the first name, last name, and date of birth match before merging. The rules for triggering a merge can be stored within the data storage system 114 and can vary based on user preference. Additionally, the rules for merging mortality data sets with healthcare data sets (as discussed with respect to step 212 of FIG. 2) can include the same rules or a varied combination of those rules.

In accordance with an example embodiment of the present invention, the other data sources 302N (e.g. lifestyle, household, credit, CDC, etc.) not related to mortality records are also merged within the mortality data sets with PII 304 to improve the specificity of the mortality data sets with PII 304. Specifically, different data sources 302N are used to add records related to mortality information and different data sources are used to add personally identifiable information to yield the merged mortality data sets with PII 304. For example, SSDMF and the obituary data can contain data fields for first name, last name, date of birth, date of death, cause of death, city of death, city of residency, etc. and lifestyle data sources can include data fields such as gender, nationality, name associations (e.g., nicknames), locations, date of birth, etc. As would be appreciated by one skilled in the art, the other data sources 302N can include a combination of PII/PHI information and non-PII/PHI information. In accordance with an example embodiment of the present invention, the data records from the lifestyle sources is used to determine the frequency of first names and their association with a particular gender to add in a gender to the data set when it is missing from the core mortality data set. For example, Peter is always a male name (as indicated by the lifestyle data source) and thus all death index records with a first name of Peter are determined to be male. In contrast, the name Pat can be male or female and thus death index records with a first name of Pat will be a percentage male and percentage female as indicated by the lifestyle data source. In such instances (e.g., when a name can be associated with a male or female) one data record may be created for each gender resulting in two separate data records. As would be appreciated by one skilled in the art, the PII data provided within the lifestyle data sources can either be factual, or inferred. For example, a factual gender can be added from census data or an inferred gender can be added by looking at the first name of the individual.

The result of the data merging process 300 is a plurality of mortality data sets with PII 304 including a more complete set information provided for deceased individuals associated with the merged mortality data sets with PII 304. Traditionally, mortality data sources 302a, 302b, 302c are incomplete and contain errors and omissions. By including multiple data sources to fill gaps in the source information, the process 300 adds more information upon which algorithms can be applied (as discussed with respect to FIGS. 2 and 4-6). In particular, matching an individual in one data set to an individual in another data set is limited by the specificity of the personally identifiable information (PII) contained in each data set (e.g., mortality data sets with PII 304 and a healthcare data set) from which the unique encrypted person tokens are derived. If little data is reported about the individual in either data set, then the chances are high that multiple individuals will match that data set. If the information about an individual is abundant and specific in a data set, then chances are high that only one unique person will match that data set. Accordingly, the significance of adding data from non-mortality data sources (e.g. such as using lifestyle data to add gender) is that the specificity added to mortality data sets with PII 304 through the lifestyle data sources increases the accuracy of a match of an individual associated with the mortality data sets with PII 304 with individuals in healthcare data sets.

Figure 4:
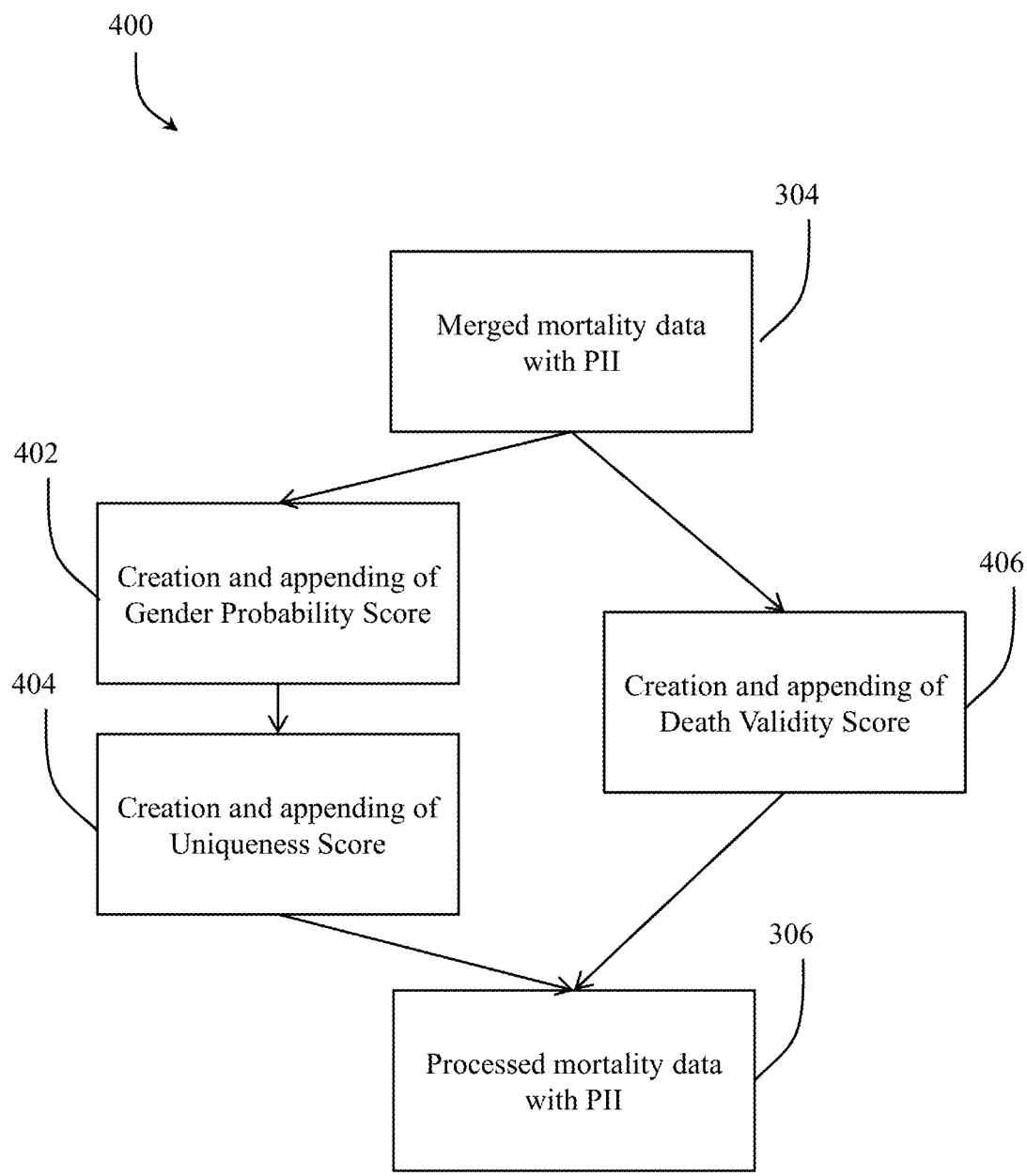
FIG. 4 is a flowchart depicting the creation and appending of algorithmic scores for death validity score and uniqueness score to mortality data sets in accordance with the present invention.

FIG. 4 illustrates an example embodiment of the process 400 for the addition of algorithmically-generated data to the mortality data sets with PII 304 to create processed mortality data sets with PII 306. In accordance with an example embodiment of the present invention, a unique combination of steps is performed to add two additional data fields to the mortality data sets with PII 304. Two data fields are added in steps 404 and 406 of the process 400. In particular, at step 404 a uniqueness score is included within the mortality data sets with PII 304 and at step 406 a death validity score within the mortality data sets with PII 304 to create the processed mortality data sets with PII 306. The uniqueness score value and the death validity score act as confidence indicators for each the processed mortality data sets with PII 306 as to how likely the information is reliable. The uniqueness score indicates a likelihood that the unique encrypted person token for a given mortality data set is unique. The death validity score indicates a confidence value that an individual associated with a given mortality data set is actually deceased. In accordance with an example embodiment of the present invention, a gender probability score based on a determination as to whether an individual token is associated with a male or female (e.g., based on a first name) is included within the process 400. The gender probability score utilizes gender information from the population data and social data to improve a statistical match of individual mortality data records with the appropriate individuals, thus impacting the accuracy of the uniqueness score. As would be appreciated by one skilled in the art, multiple different algorithms can be included within process 400 to further augment the mortality data sets with PII 304 with other characterizing data, supporting information, and/or confidence scores.

In accordance with an example embodiment of the present invention, at step 402 a gender probability score is created. In the gender probability score process of step 402, a token is created for both genders for each individual in which a gender is unknown. The gender probability score is added to each of those records. Records with a probability of 0% (e.g., no person with that name ever is that gender) are removed. The gender probability score determination is performed by matching a first name of an individual against the population data (that contains known genders) and reporting back the percentage of records in the population data that had a male gender associated with the name or a female gender associated with the name.

In accordance with an example embodiment of the present invention, at step 404, the uniqueness score is determined by the de-identification system 102 executing a specific combination of steps utilizing information from the various data sources, stored in the storage system 114. The specific combination of steps for determining the uniqueness score includes extracting identification information from each of the mortality data sets with PII 304 (e.g., associated with identifiable individuals) and querying the identification information against a population data set. The population data set can include any compilation of data about a population of individuals from any combination of data sources. For example, the population data can include data from the aggregated mortality records or any other large data set representing the population. The specific combination of steps for determining the uniqueness score also includes the de-identification system 102 identifying matches (e.g., resulting from the querying) of the identification information occurring within the population data set. Thereafter, the de-identification system 102 implements an algorithm to calculate the uniqueness score. The uniqueness score is calculated by dividing one by the number of identified matches between the identification information in the mortality data set and the population data. The result of the calculation is appended to the mortality data set with PII 304 as a uniqueness score. This specific process of step 404 is performed for each individual mortality data set within the plurality mortality data sets with PII 304 (e.g., from process 300 of FIG. 3). An example implementation of the process for step 404 is discussed in greater detail with respect to FIG. 5.

In accordance with an example embodiment of the present invention, at step 406, the death validity score is determined by the de-identification system 102 executing a specific combination of steps utilizing information from the various data sources, stored in the storage system 114. The specific combination of steps for determining the death validity score includes analyzing the mortality data sets with PII 304 associated with identifiable individuals and identifying matches of the identification information occurring within other individual mortality data sets with PII 304 for the same individual. The specific combination of steps for determining the death validity score also includes the de-identification system 102 identifying a total number of indications of an identifiable individual as being deceased. Thereafter, the de-identification system 102 implements an algorithm to calculate the death validity score. For example, the death validity score can be calculated by dividing the total number of indications of an identifiable individual as being deceased by a total number of matches for the identifiable individual occurring within the mortality data sets. The division calculation provides a probability percentage of the at least one data source that indicates that the identifiable individual is deceased. In another example, the death validity score can be calculated following the steps provided in process 600 depicted in FIG. 6. In an optional step, the de-identification system 102 can transform the probability percentage into a probability level based on the probability percentage, the probability level having a non-quantitative descriptive range. For example, for a probability of 90% or higher, the non-quantitative descriptive value would be "very high". As would be appreciated by one skilled in the art, the non-quantitative descriptive range can include any combination of descriptions (e.g., very low, low, medium, high, very high, etc.) matches with any combination of percentages. The result of the calculation/transformation is appended to the mortality data set with PII 304 as a death validity score. The specific process of step 406 is performed for each individual mortality data set within the plurality mortality data sets with PII 304 (e.g., from process 300 of FIG. 3). An example implementation of the process for step 406 is discussed in greater detail with respect to FIG. 6.

Figure 5:
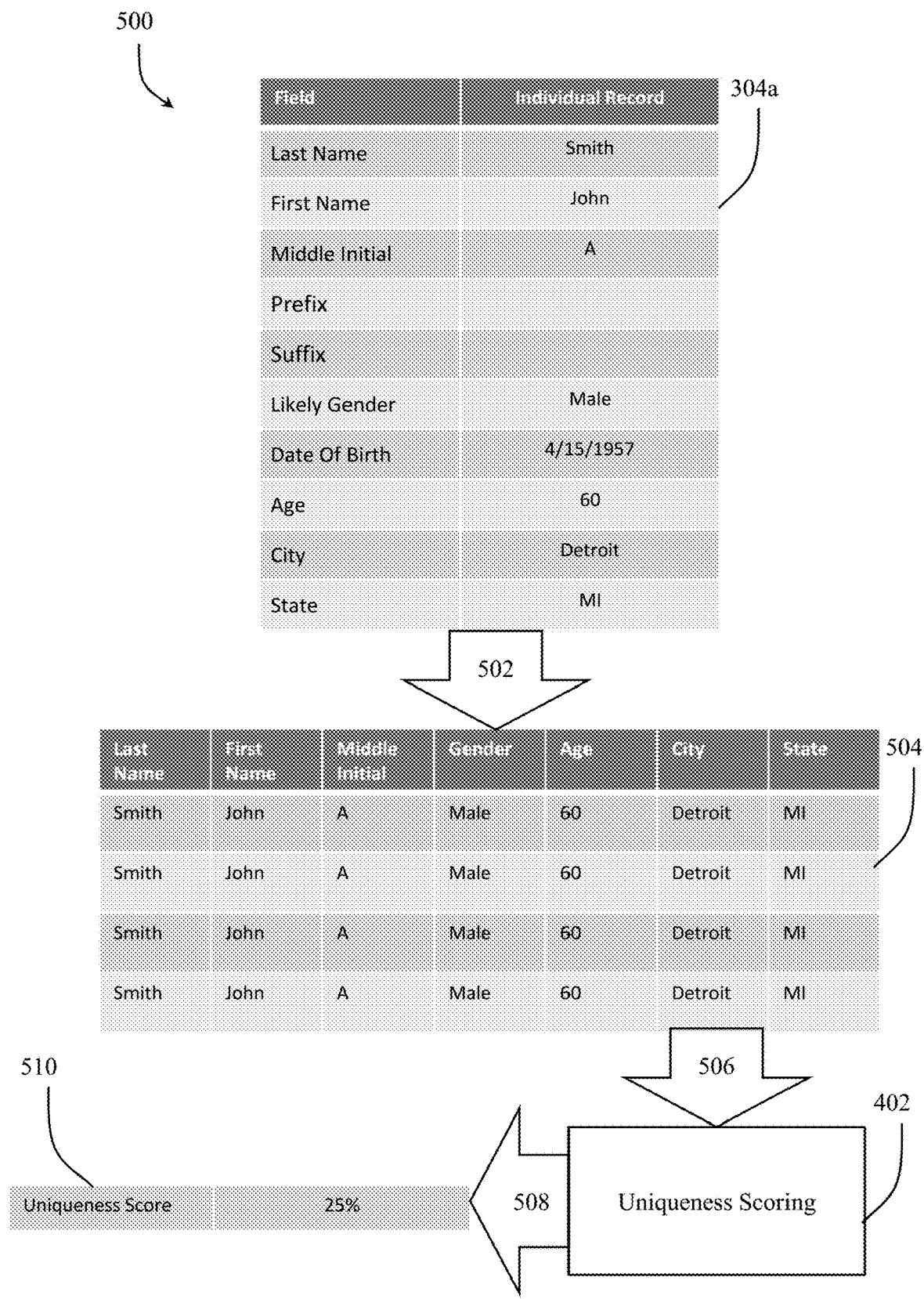
FIG. 5 is a flowchart depicting the process of creating a uniqueness score for mortality data sets in accordance with the present invention.

FIG. 5 illustrates an example process 500 of the unique combination of steps that produce the uniqueness score 510. The process 500 begins with an individual mortality data set with PII 304a. The individual mortality data set with PII 304a provided in FIG. 5 includes and/or is concerned with data fields of Last Name, First Name, Middle Initial, Prefix, Suffix, Likely Gender, Date of Birth, Age, City, and State. As would be appreciated by one skilled in the art, the individual mortality data set with PII 304a can include any combination of data fields that may be useful in accordance with the present invention. As discussed with respect to FIGS. 2 and 3, each of the data fields for the individual mortality data set with PII 304a is a result of a merge operation between a plurality of data sources (e.g., SSDMF, lifestyle data, etc.). Additionally, as shown in FIG. 5, all of the fields in the example individual mortality data set with PII 304 may not populated (e.g., Prefix and Suffix) due to missing information from the source records.

The process 500 takes the relevant fields within the individual mortality data sets with PII 304a, at step 502, and compares the data fields therein to corresponding data fields within a larger representative population data set 504 (e.g., all stored mortality data records with PII, healthcare data records, public data records, etc.) to find matching records. For example, the PII for individual associated with the mortality data set with PII 304a are used as inputs to query a dataset of the larger representative population for matches. In the example provided by FIG. 5, the individual mortality data set with PII 304a includes PII for John A. Smith, male, born on Apr. 15, 1957 from Detroit, Mich. which matches four individuals possessing the same PII in the population data set 504. At step 506 the uniqueness score 510 is calculated based on the number of matches in the population data set, as discussed with respect to FIG. 4. At step 508 the resulting uniqueness score 510 is appended to the individual mortality data set with PII as a probability that an individual matching that record is the correct individual ("25%", or "1 in 4") and/or as a qualitative label (e.g. "moderate uniqueness"). As discussed herein, each individual data record within each data set of the plurality of mortality data sets with PII 304a is evaluated by the algorithm to determine the uniqueness score 510 for each data set (to be appended to that data set).

The example process 500 provided in FIG. 5 is an example of the de-identification system 102 making probabilistic matches based on the uniqueness (specificity) of the information known about an individual between two or more data sets. For probabilistic matches, the uniqueness score 510 provides users with a metric to assist in understanding how likely it is that the individual who is deceased from the mortality data sets is the same individual in the matched healthcare data set. In accordance with an example embodiment of the present invention, the de-identification system 102 can utilize the process 500 to make deterministic matches if data fields in each data set include a unique value that is uniquely associated with an individual (e.g., social security number). In the case of deterministic matches, the uniqueness score 510 would be 100%. As would be appreciated by one skilled in the art, the uniqueness score 510 can be derived using any algorithm that takes all personally identifiable information data in the mortality data sets with PII 304 as inputs to judge how likely an individual is to be unique in the entire population (probabilistic or deterministic).

Figure 6:
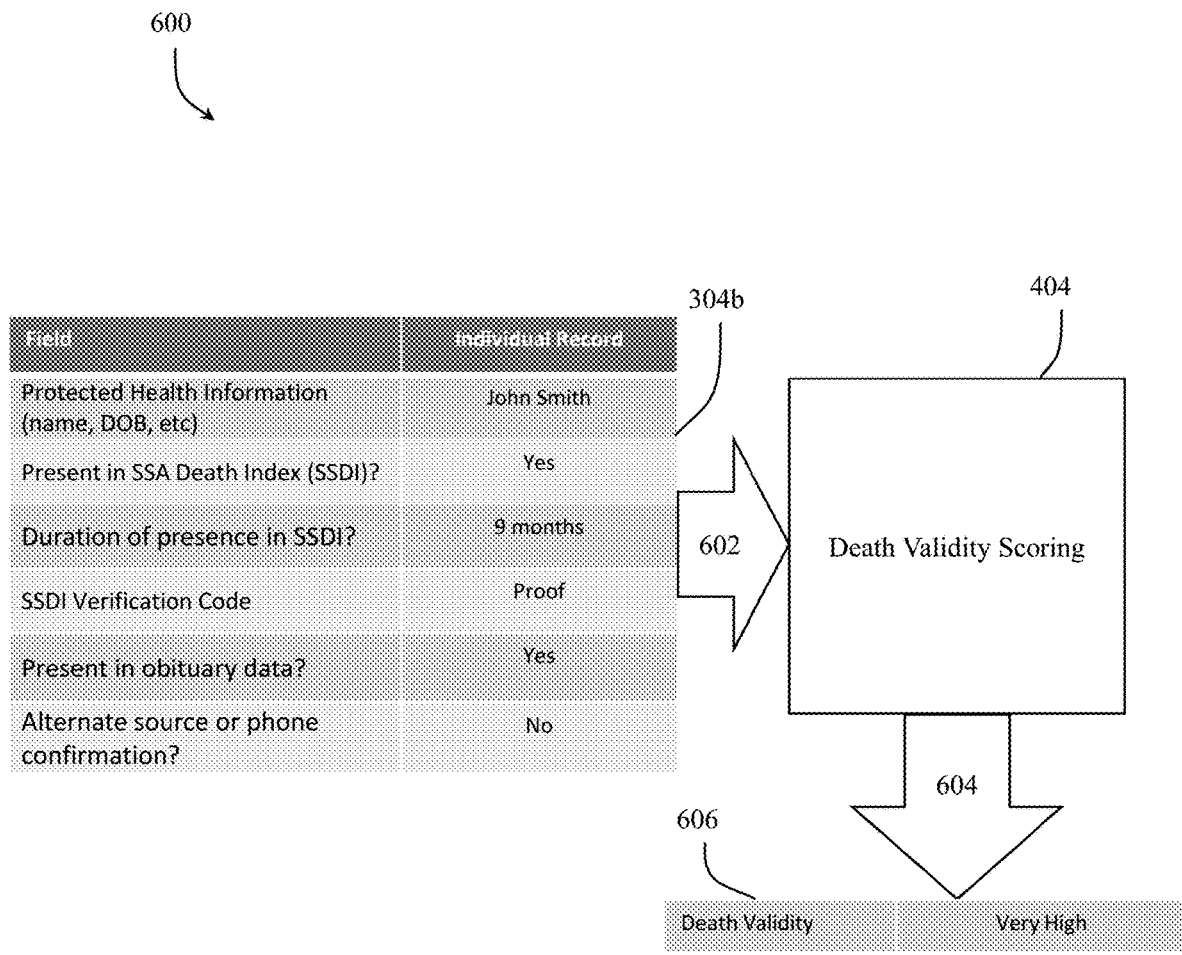
FIG. 6 is a flowchart depicting the process of creating a death validity score for mortality data sets in accordance with the present invention.

FIG. 6 illustrates an example process 600 of the unique combination of steps that produce the death validity score 606. The process 600 begins with an individual mortality data set with PII 304b. The individual mortality data set with PII 304b provided in FIG. 6 includes and/or is concerned with data fields for PII (e.g., name, date of birth, etc.), present within the SSDMF, duration of presence in the SSDMF, a SSDMF verification code (if available), presence in obituary data, and an alternate source or phone confirmation status. The example individual mortality data set with PII 304b of FIG. 6 depicts a PII for John Smith, an indication of presence in the SSDMF for 9 months with proof verification. The example individual mortality data set with PII 304b of FIG. 6 also depicts a presence in the obituary data without an alternate source or phone confirmation status. As discussed with respect to FIGS. 2 and 3, each of the data fields for the individual mortality data set with PII is a result of a merge operation between a plurality of data sources (e.g., SSDMF, lifestyle data, etc.).

At step 602 the de-identification system 102 takes the relevant fields in the individual mortality data sets with PII 304b and inserts them as inputs to calculate the death validity score 606. For example, the de-identification system 102 can utilize the inputs in a probabilistic approach to derive a probability level that the indication that an individual is deceased is valid, as discussed with respect to step 406 of process 400 depicted in FIG. 4. In accordance with an example embodiment of the present invention, the death validity score 606 (how likely an individual is to actually being deceased) can be derived through a deterministic methodology utilizing a rule based algorithm. In particular, in the example process 600 provided in FIG. 6, if an individual is flagged as deceased in both the SSDMF and obituary data fields, then the death validity score 606 field is populated with "very high" probability that the individual is dead, as shown in FIG. 6. Continuing the rule based example, if an individual is flagged as deceased only in the SSDMF data field with "Proof" flag or "Verified" flag, then the death validity score 606 indication is "high". In the last step in the rule based example, if an individual is flagged as deceased only in one data set and neither of the aforementioned SSDMF flags nor the death validity score 606 is populated then the death validity score 606 indication is "medium". At step 604 the death validity score 606 indication (e.g., low, medium, high, very high) is appended to the death validity score. As would be appreciated by one skilled in the art, each mortality data set is evaluated by the death validity score 606 algorithm, the death validity score 606 is populated, and then appended to that individual mortality data set.

In accordance with an example embodiment of the present invention, the application of processes 500 and 600 to the mortality data sets with PII 304, as discussed in greater detail with respect to FIGS. 5 and 6 create the processed mortality data sets with PII 306, as discussed in greater detail with respect to FIG. 4. Once the mortality data sets with PII 304 have been appended with the uniqueness score 510 and the death validity score 606 it has been fully processed and is ready to be de-identified to remove all PII information. Additionally, as part of the de-identification process, unique anonymous person tokens are added to the processed mortality data sets with PII 306 to enable linking de-identified individuals across data sets (e.g., healthcare data sets) to create a de-identified mortality data set 706, without exposure of PII of the de-identified individual.

Figure 7:
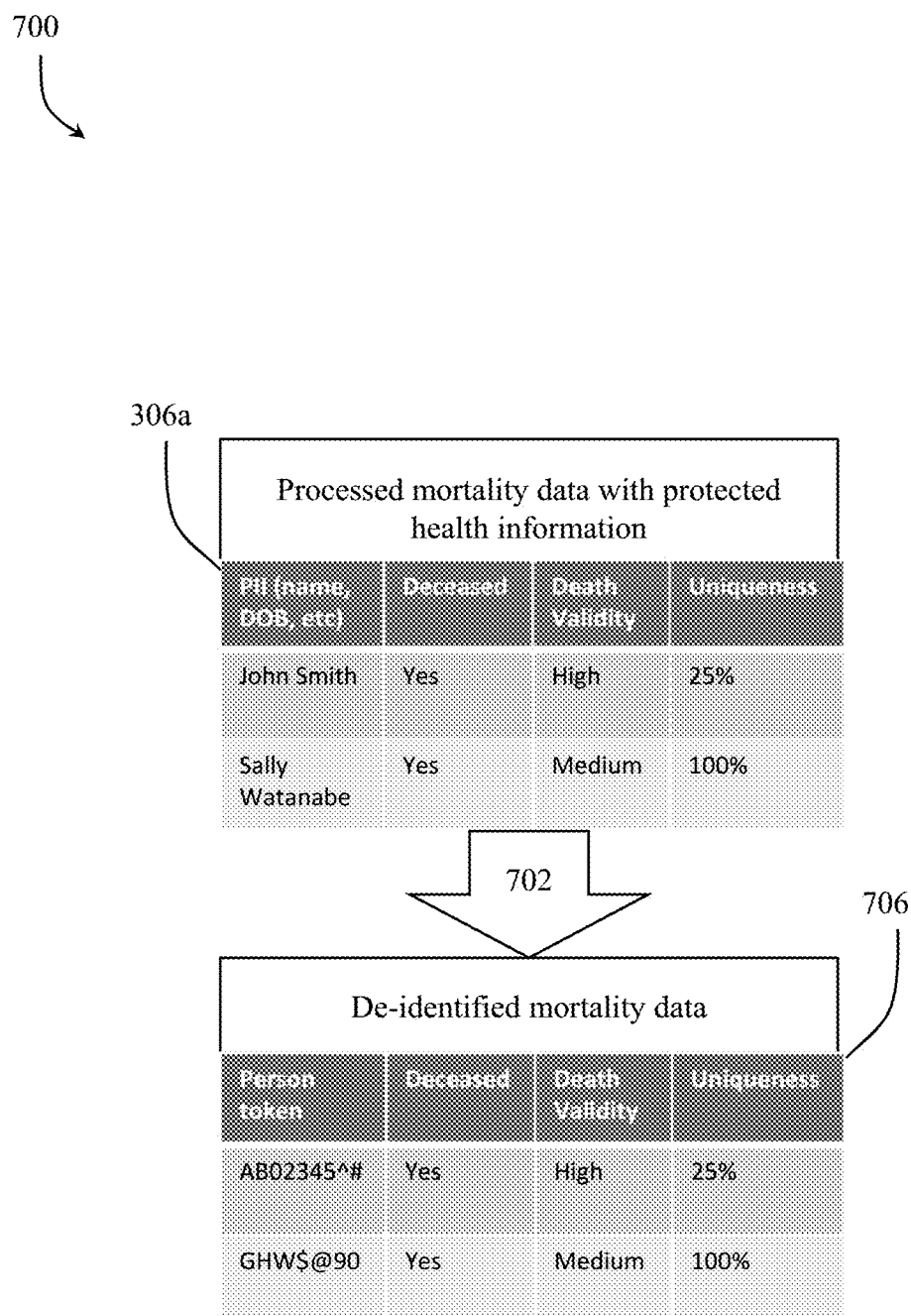
FIG. 7 is a flowchart depicting the removal of personally identifiable information from and tokenization of mortality data sets in accordance with the present invention.

FIG. 7 illustrates an exemplary process 700 for removing the personally identifiable information (PII) from the processed mortality data sets with PII 306, as discussed in greater detail with respect to FIGS. 2 and 4, and creating the unique anonymous person tokens. In accordance with an example embodiment of the present invention, the process 700 starts with the processed mortality data sets with PII 306 including with data fields for PII (e.g., name, date of birth, etc.), deceased status, death validity score, and uniqueness score. In the example depicted in FIG. 7, the processed mortality data sets with PII 306a include two entries for two individual mortality data sets. The first entry of the processed mortality data sets with PII 306a include PII of "John Smith", a deceased status of "yes", a high death validity score, and a uniqueness score of 25%. The second entry of the processed mortality data sets with PII 306a include PII of "Sally Watanabe", a deceased status of "yes", a medium death validity score, and a uniqueness score of 100%.

At step 702 the de-identification module 118 initiates the de-identification process, as discussed with respect to step 210 of FIG. 2. In particular, the de-identification process includes removing all PII from the processed mortality data sets with PII 306 and creating and appending a unique anonymous person token to the processed mortality data sets with PII 306. As would be appreciated by one skilled in the art, the unique encrypted person token is unique to the individual in whom the data set was previously associated with, as discussed in U.S. patent application Ser. No. 15/045, 605 filed on Feb. 17, 2016, incorporated herein by reference.

In the example depicted in FIG. 7, the PII entries of "John Smith" and "Sally Watanabe" are removed and unique encrypted person tokens of "AB02345^#" and "GHW$@90" are respectively appended. The unique encrypted person tokens "AB02345^#" and "GHW$@90" are unique to the individuals "John Smith" and "Sally Watanabe", respectively, such that any other data sets associated with "John Smith" or "Sally Watanabe" that are de-identified and tokenized using the de-identification system 102 of the present invention will include matching unique encrypted person tokens of "AB02345^#" and "GHW$@90", respectively. In other words, as an example, the same occurrence of first name, last name, gender, and date of birth produce the same token, no matter which data set it is found within (e.g., mortality data set, healthcare data set, population data set, etc.). As would be appreciated by one skilled in the art, depending on the PII data stored in the data set, multiple unique encrypted person tokens can be created for an individual data set, or just a single token can be created. For example, the de-identification module 118 can create a single token for an individual where there is a clear gender likelihood based on first name, but can create two tokens (one for each gender) where gender likelihood is not definitive. If two tokens are created for a data set, then the data set can be matched to other data sets matching either of the unique encrypted person tokens. Furthermore, the system can be configured to handle tokens of different character string length, e.g., 44 characters, 9 characters, or other desired character lengths as would be understood by those of skill in the art.

The result of the de-identification and tokenization at step 702 is de-identified mortality data sets 706. The unique encrypted person tokens in the de-identified mortality data sets 706 can be linked to unique encrypted person tokens added to other data sets (e.g., healthcare data sets) such that the same de-identified individual can be found in both data sets without ever exposing the originating PII, as discussed with respect to step 212 of FIG. 2. In accordance with an example embodiment of the present invention, the process 700 can include additional processing steps. For example, the process 700 can include an encryption step for the de-identified mortality data sets 706. Additionally, the unique encrypted person tokens can be created from a hash function applied to the original PII/PHI data set and encrypted. An example of the hash function is discussed in greater detail with respect to U.S. patent application Ser. No. 15/045,605 filed on Feb. 17, 2016, incorporated herein by reference. The de-identification system 102 can utilize a combination of encryption methods known in the art. Additionally, because each user can have their own token scheme derived from the same unique encrypted person token, the de-identification system 102 can re-encrypt the token according to who will be receiving the data. For example, mortality data sets delivered to Company A can be transformed to match Company A's tokens.

Figure 8:
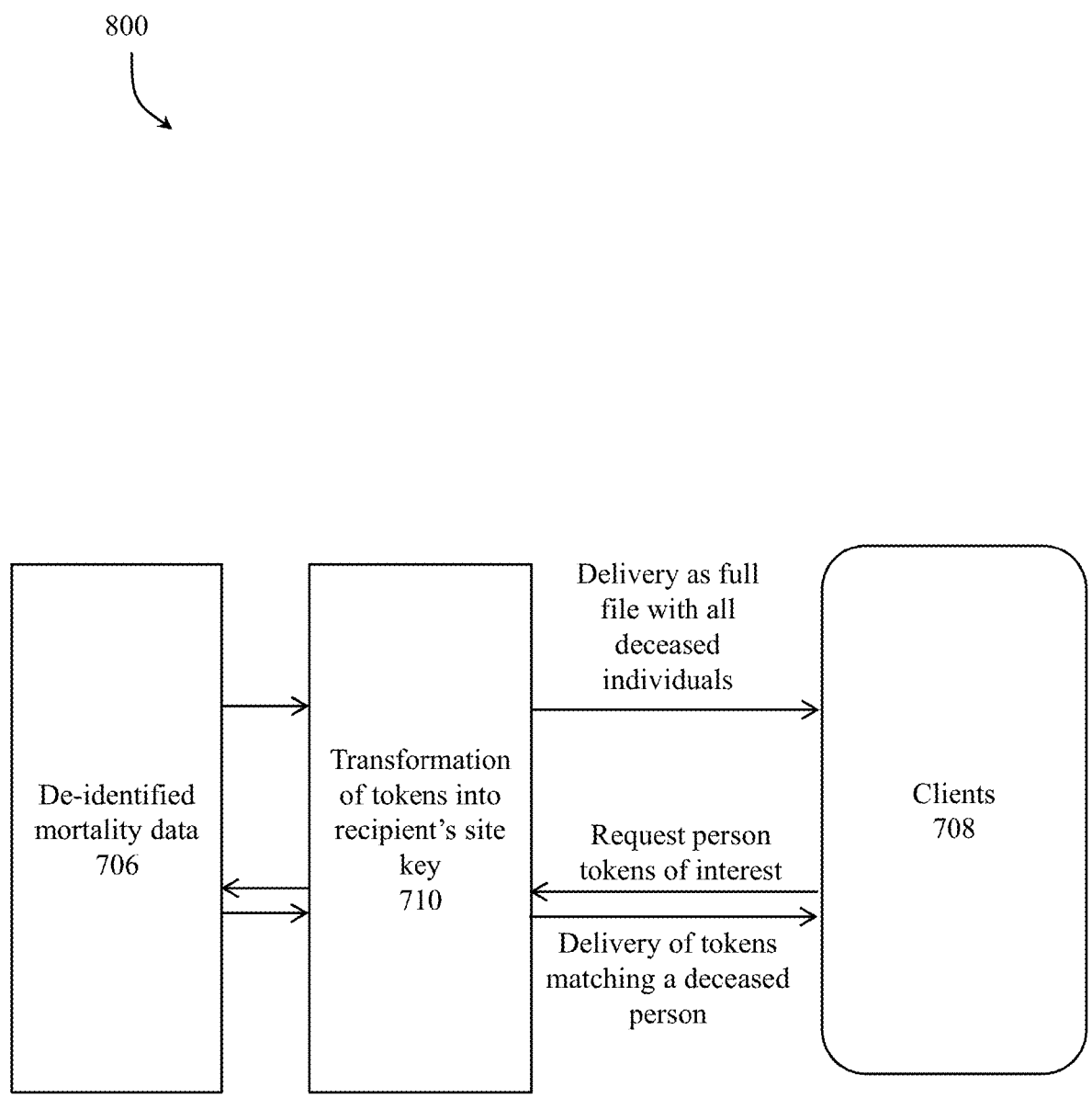
FIG. 8 is a flowchart depicting the removal of personally identifiable information, tokenization, and delivery of mortality information to clients in accordance with the present invention.

FIG. 8 illustrates the different delivery formats and processes 800 for delivering the de-identified mortality data sets 706 to requesting clients 708 (e.g., user devices 122). As would be appreciated by one skilled in the art, the de-identification system 102 can deliver the de-identified mortality data sets 706 to requesting clients utilizing any combination of systems and methods known in the art. For example, the de-identified mortality data sets 706 can be delivered as a batch file containing all individuals who are deceased or the de-identified mortality data sets 706 can be delivered in a format containing only selected deceased individuals through a two-step process. The two-step process starts with the client transmitting a list of unique person tokens (previously created by the de-identification system 102) for which they want to know the deceased status. In response to receiving the list of unique encrypted person tokens, the de-identification system 102 matches the received unique encrypted person tokens against the unique encrypted person tokens in the de-identified mortality data sets 706 stored within the storage system 114. The de-identification system 102 transmits back a list of unique encrypted person tokens that are identified as deceased (e.g., mortality data sets matching the unique encrypted person tokens from the client). Additionally, the system can provide the death validity score 606 and the uniqueness score 510 for each identified unique encrypted person token. As would be appreciated by one skilled in the art, the list of unique encrypted person tokens can be transmitted to the system utilizing any methods and systems known in the art. For example, the unique encrypted person token list can be transmitted through a file exchange process (input file from client with tokens of interest, output file from the de-identification system 102 with matching tokens that are deceased). In another example, the unique encrypted person token list can be transmitted through an API process where a query string(s) is sent from the client with the token(s) of interest, and a result string(s) is returned from the de-identification system 102 on the deceased status (including death validity score 606 and the uniqueness score 510). Additionally, as would be appreciated by one skilled in the art, the data can be delivered to clients through different channels (sFTP, email, etc.), in whole or in subset, with or without a matching process to the clients' tokens of interest, with different frequencies, in combination with other data sets outside of the mortality data, and a number of other formats and through a number of different processes.

In accordance with an example embodiment of the present invention, FIG. 8 includes a token transformation process 710 as an interim step in the process 800 of delivering the full data file to a client 708 in their site-specific tokens. For the pull method, clients transform their tokens using process 710, look them up in the de-identified mortality data 706, and then transform the matching tokens back into client's tokens using process 710 before delivering. In all cases, the tokens being transmitted from one party to another must pass through the token transformation process 710 in which tokens in the site-key of the sender are converted into the token key of the recipient to allow matching to their token set. This token conversion process is described in U.S. patent application Ser. No. 15/045,605, which is incorporated herein by reference.

Figure 9:
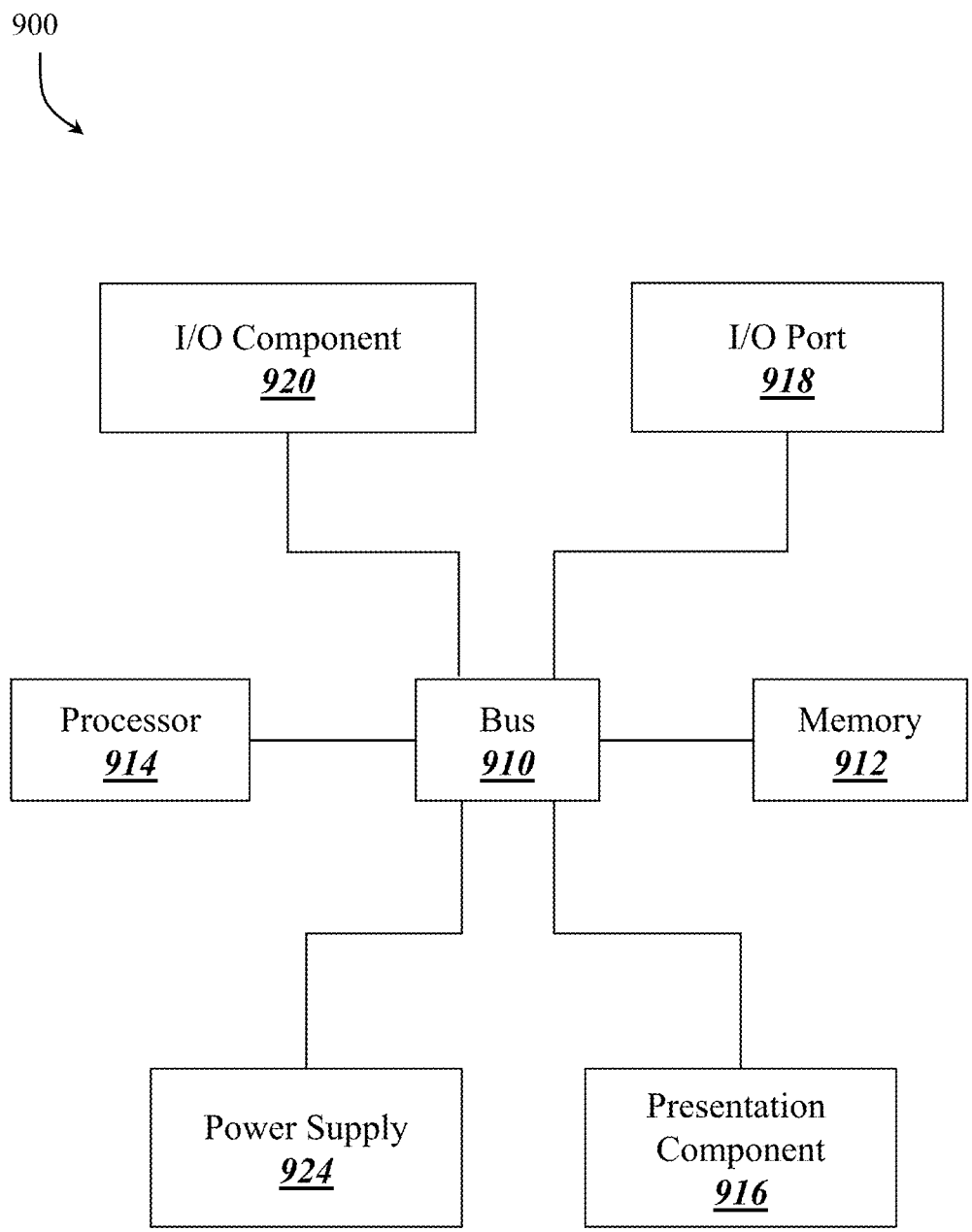
FIG. 9 is a diagrammatic illustration of a high level architecture for implementing processes in accordance with aspects of the invention.

Any suitable computing device can be used to implement the computing devices 104, user devices 122, and methods/functionality described herein and be converted to a specific system for performing the operations and features described herein through modification of hardware, software, and firmware, in a manner significantly more than mere execution of software on a generic computing device, as would be appreciated by those of skill in the art. One illustrative example of such a computing device 900 is depicted in FIG. 9. The computing device 900 is merely an illustrative example of a suitable computing environment and in no way limits the scope of the present invention. A "computing device," as represented by FIG. 9, can include a "workstation," a "server," a "laptop," a "desktop," a "hand-held device," a "mobile device," a "tablet computer," or other computing devices, as would be understood by those of skill in the art. Given that the computing device 900 is depicted for illustrative purposes, embodiments of the present invention may utilize any number of computing devices 900 in any number of different ways to implement a single embodiment of the present invention. Accordingly, embodiments of the present invention are not limited to a single computing device 900, as would be appreciated by one with skill in the art, nor are they limited to a single type of implementation or configuration of the example computing device 900.

The computing device 900 can include a bus 910 that can be coupled to one or more of the following illustrative components, directly or indirectly: a memory 912, one or more processors 914, one or more presentation components 916, input/output ports 918, input/output components 920, and a power supply 924. One of skill in the art will appreciate that the bus 910 can include one or more busses, such as an address bus, a data bus, or any combination thereof. One of skill in the art additionally will appreciate that, depending on the intended applications and uses of a particular embodiment, multiple of these components can be implemented by a single device. Similarly, in some instances, a single component can be implemented by multiple devices. As such, FIG. 9 is merely illustrative of an exemplary computing device that can be used to implement one or more embodiments of the present invention, and in no way limits the invention.

The computing device 900 can include or interact with a variety of computer-readable media. For example, computer-readable media can include Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices that can be used to encode information and can be accessed by the computing device 900.

The memory 912 can include computer-storage media in the form of volatile and/or nonvolatile memory. The memory 912 may be removable, non-removable, or any combination thereof. Exemplary hardware devices are devices such as hard drives, solid-state memory, optical-disc drives, and the like. The computing device 900 can include one or more processors that read data from components such as the memory 912, the various I/O components 916, etc. Presentation component(s) 916 present data indications to a user or other device. Exemplary presentation components include a display device, speaker, printing component, vibrating component, etc.

The I/O ports 918 can enable the computing device 900 to be logically coupled to other devices, such as I/O components 920. Some of the I/O components 920 can be built into the computing device 900. Examples of such I/O components 920 include a microphone, joystick, recording device, game pad, satellite dish, scanner, printer, wireless device, networking device, and the like.

As utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about", "generally", and "approximately" are intended to cover variations that may existing in the upper and lower limits of the ranges of subjective or objective values, such as variations in properties, parameters, sizes, and dimensions. In one non-limiting example, the terms "about", "generally", and "approximately" mean at, or plus 10 percent or less, or minus 10 percent or less. In one non-limiting example, the terms "about", "generally", and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A method for providing de-identified mortality indicators in healthcare data, the method comprising:
   aggregating, using a computing device, mortality data records associated with identifiable individuals from at least one data source;
   merging, using the computing device and at least one data structure, the aggregated mortality data records into mortality data sets each associated with identifiable individuals;
   assigning, using the computing device, a uniqueness score to each mortality data set;
   assigning, using the computing device, a death validity score to each mortality data set;
   de-identifying, using the computing device with data comprising the uniqueness score and the death validity score, the mortality data sets by removing protected health information and personal identification information within the mortality data sets and associating each mortality data set previously associated with an identifiable individual with a unique encrypted person token, which is unique to each individual of the identifiable individuals;
   receiving, using the computing device, previously de-identified healthcare data sets with the unique encrypted person tokens associated therewith;
   merging, using the computing device, the de-identified mortality data sets with the previously de-identified healthcare data sets with the unique encrypted person tokens associated therewith;
   storing, merged de-identified healthcare data sets in a location segregated from protected health information and personal identification information; and
   delivering, using the computing device, the merged de-identified healthcare data sets stored in the location comprising the encrypted tokens in place of protected health information and personal identification information, wherein delivering of records associated with identifiable individuals is prevented.

2. The method of claim 1, wherein the merging comprises matching the unique encrypted person tokens of de-identified mortality data sets with the unique encrypted person tokens of the previously de-identified healthcare data sets.

3. The method of claim 1, wherein each of the de-identified mortality data sets comprise the unique encrypted person token, the indicator of mortality, the uniqueness score, and the death validity score.

4. The method of claim 3, wherein each of the mortality data sets further comprises a cause of death indicator.

5. The method of claim 3, wherein each of the mortality data sets further comprises a gender probability score.

6. The method of claim 3, wherein:
the uniqueness score indicates a likelihood that the unique encrypted person token for a given mortality data set is unique; and
the death validity score indicates a confidence value that an individual associated with a given mortality data set is actually deceased.

7. The method of claim 6, wherein determining the uniqueness score comprises:
extracting identification information from the mortality data sets associated with identifiable individuals;
querying the identification information against a population data set and a social data set;
identifying matches of the identification information occurring within the population data set or the social data set;
calculating the uniqueness score by dividing one by the number of identified matches; and
appending the uniqueness score to a mortality data set associated with the individual.

8. The method of claim 6, wherein determining the death validity score comprises:
analyzing mortality data sets associated with identifiable individuals;
identifying matches of the identification information occurring within the mortality data sets;
identifying a total number of indications of an identifiable individual as being deceased;
dividing the total number of indications of an identifiable individual as being deceased by a total number of matches for the identifiable individual occurring within the mortality data sets to determine a probability percentage of the at least one data source that indicates that the identifiable individual is deceased; and
appending the probability percentage to a mortality data set of the mortality data sets that is associated with the individual as the death validity score for the individual.

9. The method of claim 6, wherein determining the uniqueness score comprises a rule based function that transforms a probability percentage into a probability level based on the probability percentage, the probability level having a non-quantitative descriptive range.

10. The method of claim 1, wherein the at least one data source includes one or more of a social security death master file, a lifestyle data for gender, and obituary data.

11. The method of claim 1, wherein the death validity score is a quantitative statistical score.

12. The method of claim 1, wherein the death validity score is a qualitative flag.

13. The method of claim 1, wherein delivering of records associated with identifiable individuals is prevented further comprises segregating de-identified and tokenized data sets from any data base or data storage containing identifiable information by storing in a specialized database for de-identified and tokenized data sets only and encoding access and permission restrictions allowing transmission requested data from the specialized database only.

14. A system comprising:
a computing device;
one or more databases containing previously de-identified healthcare data sets with encrypted person tokens;
a data aggregation module configured to aggregate data records with protected health information included therein from a plurality of data sources;
a merging module configured to transform all of the data records associated with identifiable individuals into mortality data sets, each of the mortality data sets uniquely associated with each of the identifiable individuals;
a de-identification module configured to:
remove the protected health information from the mortality data sets to create de-identified mortality data sets; and
create the encrypted person token based on the removed protected health information, wherein the encrypted person token is uniquely associated with an individual previously associated with the removed protected health information;
the merging module configured to merge the de-identified mortality data sets with de-identified healthcare data sets based on matching the encrypted person tokens associated therewith; and wherein resulting merged data sets include an indicator of mortality, a match probability score giving a likelihood that the unique person token is unique, and a death validity score giving a measure of confidence that the person is actually deceased stored in a location segregated from protected health information and personal identification information, wherein delivering of records associated with identifiable individuals is prevented.

15. The system of claim 14, further comprising isolating de-identified and tokenized data sets from any data base or data storage containing identifiable information by storing in a specialized database for de-identified and tokenized data sets only and encoding access and permission restrictions allowing transmission requested data from the specialized database only.

16. A system, comprising:
a computing device;
one or more databases containing data sets comprising:
de-identified mortality data sets with protected health information removed, wherein the de-identified mortality data sets have an association with each mortality data set previously associated with an identifiable individual with a unique encrypted person token, which is unique to each individual of the identifiable individuals; and
previously de-identified healthcare data sets with the unique encrypted person tokens associated therewith;
wherein the de-identified mortality data sets are merged with the previously de-identified healthcare data sets with the unique encrypted person tokens associated therewith; and
wherein the resulting merged data sets include an indicator of mortality, a match probability score giving a likelihood that the unique person token is unique, and a death validity score giving a measure of confidence that the person is actually deceased.

\* \* \* \* \*